United States Patent [19]

Baldeschwieler

[11] Patent Number: 5,527,538
[45] Date of Patent: Jun. 18, 1996

[54] LIPOSOMAL TARGETING OF ISCHEMIC TISSUE

[75] Inventor: John D. Baldeschwieler, Pasadena, Calif.

[73] Assignee: Vestar, Inc., San Dimas, Calif.

[21] Appl. No.: 83,123

[22] Filed: Jun. 25, 1993

Related U.S. Application Data

[63] Continuation of Ser. No. 759,961, Sep. 16, 1991, abandoned, which is a continuation of Ser. No. 411,716, Sep. 25, 1989, abandoned, which is a continuation-in-part of Ser. No. 339,682, Apr. 18, 1989, abandoned.

[51] Int. Cl.$^6$ .................................................... A61K 9/127
[52] U.S. Cl. ..................................... 424/1.21; 424/450
[58] Field of Search ................................ 424/450, 1.1

[56] References Cited

U.S. PATENT DOCUMENTS

| | | | |
|---|---|---|---|
| 4,728,575 | 3/1988 | Gamble et al. | 424/1.1 |
| 4,753,788 | 5/1988 | Gamble | 424/1.1 |
| 4,873,088 | 10/1989 | Mayhew | 424/450 |
| 4,976,964 | 12/1990 | Schlossmann | 424/450 |
| 5,019,369 | 5/1991 | Presant et al. | 424/1.1 |

FOREIGN PATENT DOCUMENTS

| | | |
|---|---|---|
| 0342620 | 11/1989 | European Pat. Off. . |
| WO8807851 | 10/1988 | WIPO . |

OTHER PUBLICATIONS

Proffitt et al. J. Nuclear Medicine 24, #1, 1983, p. 45.
Gregoriadis & Senior. FEBS Letters 119, p. 43, 1980.
Caride et al Science, 198, p. 735 1977.
Mueller et al, Circulation research 49, 405, 1981.
Cole et al., Cardiovascular Research 16, 516–523 (1982).
Chemical Abstracts, vol. 109, No. 11, 12 Sep. 1988, Columbus, Ohio, US; abstract No. 85657M, D. Zang et al.: 'the distribution of liposome–encapsulated atp in experimental ishmeic myocardium' p. 11; columb 2; &zhonghua xinxeuquanbing zazhi 1988, 16(1). 48–51 (abstract).

Chemical Abstracts, vol. 112, No. 6, 5 Feb. 1990, Columbus Ohio, US; abstract No. 42426E, S. Chapat et al.: 'variations of the plasma concentration of adenosine triphosphate (atp) in experimental cerebral ischemia after the intra–carotid administration of atip liposomes' p. 432; column 2; &congr. int. technol. pharm., 5th 1989, 3 66–71 (the abstract).
Chemical Abstracts, vol. 100, No. 17, 23 Apr. 1984, Columbus, Ohio, US; abstract No. 136841R, T. N. Palmer, 'the mechanisms of liposome accumulation in infarction' p. 459; column 1; &biochim, biophys. acta 1984, 797(3), 363–8 (abstract).
Supplementary European Search Report; 02 Apr. 1992 (pp. 1–2). EP90907986.
Caride & Sostman, "Methodological Considerations for the Use of Liposomes in Diagnostic Imaging" Chap. 8 in Liposome Technology vol. II (1984) pp. 108–124.
Tumor–Imaging Potential of Liposomes Loaded with In–111–NTA: Biodistribution in Mice, Proffitt et al. 1983) J. Nucl. Med. 24, 45–51.
Liposomal Blockade of the Reticuloendothelial System: Improved Tumor Imaging with Small Unilamellar Vesicles, Proffitt et al. (1983) Science 220, 502–505.
Caride & Sostman, "Methodological Considerations for the Use of Liposomes in Diagnostic Imaging" Chap. 8 in Liposome Technology vol. II (1984) pp. 108–124.
Caride et al., Science 198, 735–738 (1977).
Mueller et al., Circulation Research 49, 405–415 (1981).
Cole et al., Cardiovascular REsearch 16, 516–523 (1982).
Leinberger et al., Microcirculation of the Heart, Springer–Verlag 98–103 (1982).

(List continued on next page.)

*Primary Examiner*—G. S. Kishore
*Attorney, Agent, or Firm*—Adam Cochran; George A. Gilbert

[57] ABSTRACT

Liposomes of a size of less than 200 nanometers target ischemic myocardial tissue and preferentially deliver active agents to infarcted areas in the absence of antibodies bound to the liposomes to effect the delivery.

4 Claims, 1 Drawing Sheet

OTHER PUBLICATIONS

Palmer et al., Bioscience Reports I, 337–344 (1981).
Caride, Adv. Cardiol. 27, 114–126 (1980).
Caride et al., J. Cardiovascular Pharmacology 6, 996–1005 (1984).
Caride et al., Clin. Res. 26, 223A (1978).
Goldman et al., J. Comput. Assist. Tomogr. 5, No. 2 (1981).
Jennings et al., Microcirculation of the Heart, Springer–Verlag 87–97 (1982).

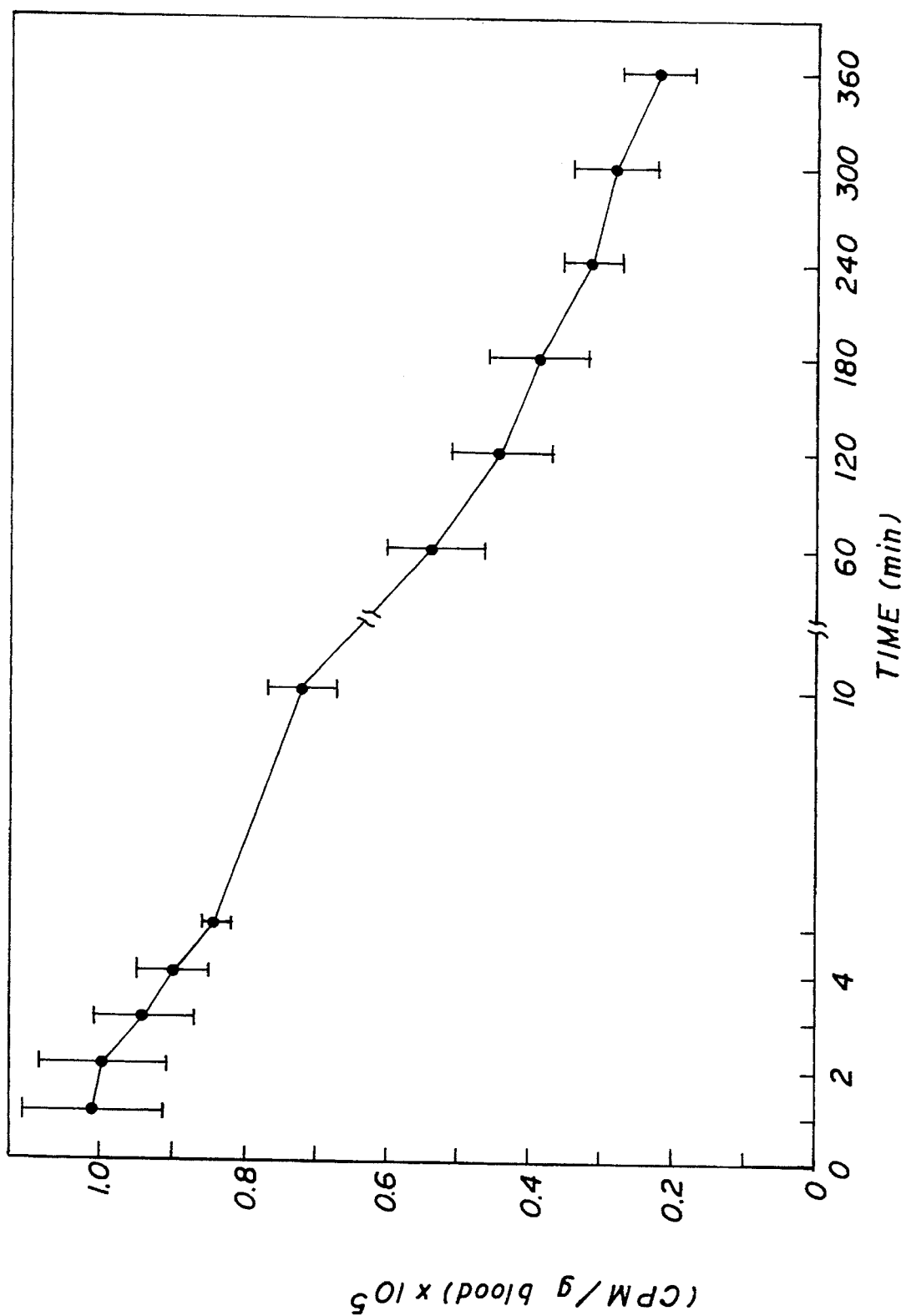

LIPOSOMAL TARGETING OF ISCHEMIC TISSUE

RELATED APPLICATION

This is a continuation of application Ser. No. 07/759,961 filed on 16 Sep. 1991, now abandoned, which is a continuation of parent application Ser. No. 07/411,716 filed on 25 Sep. 1989 now abandoned which is a continuation in part of Ser. No. 07/339,682 filed on Apr. 18, 1989 now abandoned.

FIELD OF THE INVENTION

This invention relates in general to the field of biochemistry and medicine, and more particularly to the use of liposomes in the diagnosis and treatment of ischemic tissue.

BACKGROUND OF THE INVENTION

Ischemia is a deficiency of blood in tissue, and is a significant medical problem. For example, heart disease is a leading cause of morbidity and mortality and two related conditions which are of significant concern are myocardial ischemia (tissue anemia in the heart muscle as a result of obstruction of the blood supply such as by vasoconstriction), and myocardial infarct or infarction (an ischemic condition resulting in the localized death of heart muscle and caused by the particulate obstruction of the flow of arterial blood). While progress has been made in the treatment of ischemic tissue, there is much room for improvement.

One problem with potential antiischemic agents is the action of these agents on other than ischemic tissue. For example, many potent coronary vasodilators are ineffective during myocardial ischemia because they dilate nonischemic coronary blood vessels as well as the ischemic vessels, which draws blood flow away from the ischemic zone. Additionally, many antiischemic compounds (e.g., calcium entry blockers) would be more effective if the agent could be targeted directly to the ischemic region.

Thus, it has been a desideratum to provide a drug delivery system to selectively deliver a compound into an ischemic myocardial bed, that is, deliver an active agent preferentially to infarcted heart tissue rather than nonischemic tissue. In this regard, the terms "ischemic" or "ischemia" as used herein refer to tissue in the state of traumatic tissue anemia and include infarcted tissue.

Phospholipid vesicles (liposomes) have been pursued in the hope that they would concentrate in selected tissues and result in additional enhancement in the delivery of active agents from this tissue specificity. Accordingly, workers have attempted to employ liposomes for the delivery of active agents to myocardial tissue. For example, in a publication by Caride and Zaret in Science 198, 735–738 (1977) multilamellar liposomes of approximately 1,000 nm in diameter with either net positive, negative or neutral charge were administered to mammals after the induction of embolic closed-chest interior wall myocardial infarction. The liposomes were labeled with $^{99m}$Tc-DTPA (Diethylene triamine pentaacetic acid). While this publication reports an accumulation of positive and neutral MLVs in infarcted myocardial tissue, free $^{99m}$Tc-DTPA has been shown to accumulate in ischemic myocardium (ten times that of normal myocardium after a circulation time of one hour) and further data has shown that the accumulation of $^{99m}$Tc-DTPA in infarcted myocardium observed in the subject reference was actually due to the release of vesicle contents in circulation and subsequent accumulation of free $^{99m}$Tc-DTPA in the damaged myocardium.

The publication by Mueller et al. in Circulation Research 49, 405–415 (1981) reports the use of a protein marker ($^{131}$I-albumin) retained in 400 to 700 nanometer small, unilamellar liposomes. The results show a slight accumulation of positive liposomes in ischemic myocardium compared to normal myocardium (ischemic/normal equal 1.38:1) and no net accumulation in ischemic myocardium was seen with neutral liposomes (ratio 0.81:1).

An article in Cardiovascular Research 16, 516–523 (1982) Cole et al. describes myocardial liposome uptake in the early stages of myocardial infarction and concluded that 75 to 125 nm liposomes show no evidence of preferential uptake by ischemic myocardium. The authors suggest that liposomes thus have limited potential as a means of drag delivery in myocardial infarction. Antibodies have also been covalently bound to liposomes in an attempt to deliver such vesicles preferentially to certain tissues, but the results have been less than successful in many instances.

SUMMARY OF THE INVENTION

According to the invention, a method is provided for targeting ischemic tissue in a patient, comprising introducing into the patient's bloodstream an amount of liposomes, of a size of less than 200 nm (preferably unilamellar vesicles) and preferably characterized by being comprised of chemically pure synthetic phospholipids, most preferably having aliphatic side chains of a length of at least 16 carbons, and containing a therapeutic or diagnostic agent, sufficient to preferentially deliver (i.e., target) a quantity of the agent to the ischemic tissue in the essential absence of antibodies bound to the liposomes to effect the delivery. The expression "chemically pure phospholipids" is meant to define phospholipids which are essentially free of deleterious detergent moieties and impurities which cause aggregation of small unilamellar vesicles (SUVs) formed therefrom, and which are more than 97% pure.

Preferably, the SUVs have a diameter predominantly of from 50 to 100 nm, are essentially neutral in charge, and incorporate phospholipids having a side chain length of from 16 to 18 carbon atoms. More preferably, the liposomes are prepared from distearoyl phosphatidylcholine and include cholesterol (most preferably in an amount of from 10 to 50% of total lipid) as a vesicle stabilizer.

The targeted ischemic tissue is preferably ischemic myocardial tissue such as reversibly infarcted myocardial tissue, and the method has shown efficacy in targeting active agents thereto. While I do not wish to be bound by any particular theory as to the targeting of the liposomes to acute myocardial ischemic tissue, it appears that the liposomes pass through capillaries with increased permeability (increased pore size) and can preferentially penetrate ischemic tissue, such as ischemic myocardium, relative to a nonischemic region.

A variety of diagnostic agents may be encapsulated within the liposomes and used in the method of the invention. In the examples below, a radioactive isotope of indium ($^{111}$In) is loaded into the liposomes and could permit gamma imaging of acute myocardial ischemia. In addition, appropriate liposomal NMR contrast agents such as are described in U.S. Pat. No. 4,728,575 may be administered for imaging myocardial ischemia by magnetic resonance techniques.

As to therapeutic agents, enzymes which catalyze the breakdown of superoxide or oxygen radical species (e.g., superoxide dismutase) may be incorporated into appropriate vesicles, as may therapeutic agents such as catalase or glucose oxidase, or dihydro-pyridine compounds such as nicardipine. The particular diagnostic or therapeutic agents which may be used with the invention will be apparent to those of skill in the art following disclosure of this discovery, and do not constitute part of the invention per se.

In the illustrative examples, radiolabelled liposomes are employed to delineate ischemic tissue and thus demonstrate the ability of the method of the invention to selectively deliver therapeutic or diagnostic agents to traumatized ischemic myocardium. With this disclosure, the use of additional diagnostic or therapeutic agents in connection with the treatment of myocardial ischemia or infarct will be apparent to one of skill in the art.

BRIEF DESCRIPTION OF THE DRAWING

FIG. 1 displays blood clearance data in dogs for $^{111}$In-labelled liposomes with time. Data are expressed as the radioactivity (CPM)/g blood. For each point, N=4. The values are expressed as mean±S.D.

DETAILED DESCRIPTION

Preparation of Liposomes

The liposomes which are used in the invention are small unilamellar liposomes of a size of less than 200 nm, preferably having a diameter of from 50 to 100 nm. As noted above, the vesicles are preferably comprised of chemically pure synthetic phospholipids having saturated aliphatic side chains and most preferably are prepared from phospholipids such as distearoyl phosphatidylcholine. Cholesterol is advantageously incorporated into the liposomes to increase the stability of the vesicles which are used in the disclosed process.

A wide variety of therapeutic or diagnostic agents may be incorporated in the inner aqueous space or the lipid bilayer of the liposomes by methods which will be apparent to one of skill in the art. In the following examples a chelating compound and an ionophore are employed for loading external cations for radiolabelling into the vesicles. The preferred ionophore is A23187, but other useful ionophores are polyethers such as lasalocid A(X-537A) and 5-bromo derivatives of lasalocid; cyclic depsipeptides such as beauvericin; and cyclic peptides such as valinomylin. The chelating agent is preferably nitriloacetic acid (NTA) although other chelators may also be used.

The liposomes are prepared by dissolving the phospholipid and cholesterol in an appropriate organic solvent, such as chloroform, and evaporating the solvent to form a lipid film. If, as in the following examples, an ionophore is employed to load the diagnostic or therapeutic agent into the liposomes, this compound may be added to the lipid solution before evaporation.

The dried lipid film is then hydrated in an appropriate aqueous phase, such as phosphate-buffered saline or other physiologically appropriate solution. Water soluble drugs or therapeutic agents may be contained in the hydrating solution, although if remote loading is desired a loading agent such as a chelating agent described above may be added to the hydrating solution to be encapsulated within the inner aqueous space of the liposome.

Upon the addition of the hydrating solution, liposomes of varying size spontaneously form and encapsulate a portion of the aqueous phase. Thereafter, the liposomes and suspending aqueous solution are subjected to a shear force such as sonication, or processed through a homogenizer according to the method described in U.S. Pat. No. 4,753,788; to produce vesicles within the specified size. The liposomes are then processed to remove undesirable compounds from the suspending solution, for example the chelating agent or unencapsulated drug, which may be accomplished through processes such as gel chromatography or ultrafiltration. If necessary, the product is then concentrated to remove excess buffer solution. Since the liposomes are smaller in size than 0.2 micron, they are then passed through a sterile 0.22 micron filter to remove any microorganisms which may be present in the suspension. Thereafter, the liposomes are filled into sterilized glass containers and stoppered with a sterilized elastomer closure.

EXAMPLE 1

SUVs have been prepared by formulating an organic solution of distearoyl phosphatidylcholine and cholesterol in a 2:1 molar ratio, evaporating the solution to dryness to form a lipid film, and further drying the lipid under vacuum. In order to permit the subsequent loading of the $^{111}$In into the vesicles, a divalent ionophore (A23187) was added to the lipid solution before evaporation. In a typical preparation, 20 μmoles distearoyl phosphatidylcholine, 10 μmoles cholesterol and 0.04 μmoles A23187 were dissolved in chloroform, dried to a thin film at 60° C. under a stream of nitrogen and then dried in vacuo overnight.

The dried lipid film was then hydrated with an appropriate aqueous phase, for example, phosphate-buffered saline solution (0.9% NaCl and 5 mM sodium phosphate, pH 7.4) containing a chelating agent for loading the $^{111}$In$^{3+}$, and a shear force applied to form the SUVs. In a typical preparation, the dried lipids were hydrated with phosphate-buffered saline containing 1 mM nitrilotriacetic acid (NTA) as a chelating agent, and the mixture was sonicated at approximately 65° C. until the suspension cleared (approximately five minutes) and then centrifuged at 400 g. Unencapsulated NTA was removed from the vesicles by filtering the mixture through a Sephadex G-50 column. The liposomes were determined by a Nicomp Model 270 submicron particle size analyzer to have a mean diameter less than 100 nm.

EXAMPLE 2

A 2:1 molar ratio mixture of distearoyl phosphatidylcholine and cholesterol was dissolved in chloroform, along with the ionophore A23187. These components were thoroughly mixed until completely dissolved. This solution was then placed in a rotary evaporator to remove the chloroform and deposit a lipid film on the surface of the evaporator flask. Alternatively, other known drying methods could be used to form the lipid film or powder.

The chelating material (NTA) was then mixed in phosphate buffered saline and the resulting solution was added to the lipid film. The liposomes thus formed were processed through a homogenizer, according to the process taught in U.S. Pat. No. 4,753,788 to Gamble, to produce vesicles having a mean diameter not to exceed 100 nanometers. The liposomes were then passed through a gel chromatography column to remove the chelating agent which remained in the suspending solution outside the liposomes. The product was then concentrated through a hollow fiber concentrator to remove excess buffer and to concentrate the liposome suspension.

Thereafter, the liposomes were filtered through a 0.22 micron sterile filter and transferred to sterilized glass containers in a class 100 hood and stoppered with a sterilized elastomer closure. Throughout this process, appropriate QA/QC procedures were employed to ensure sterile processing conditions.

Vesicle Loading

As noted above, the vesicles may be loaded with amphiphilic agents during lipid film formation, with aqueous-soluble agents during hydration, or by other known loading procedures. Since the targeting of the liposomes to myocardial tissue is best demonstrated by the delivery of radioactive agents, the gamma-imaging agent $^{111}$indium$^{3+}$ was loaded into the liposomes immediately prior to use.

EXAMPLE 3

Loading has been accomplished by using incubation mixtures consisting of 500 µl of vesicles, 35 µl of 3.4 µM InCl$_3$ in 104 mM sodium citrate (pH 7.4), and 1–50 µl of $^{111}$In$^{3+}$, depending on the required activity. The volume of PBS equal to twice that of the $^{111}$indium$^{3+}$ addition was included in the incubation mixture. Incubation time and temperature may be selected according to published procedures such as Mauk et al. Analytical Biochemistry 94, 302–307 (1979), which is incorporated herein by reference. Generally, the loading is performed by incubation at 60° to 80° C. for 15 to 60 minutes. The incubation is terminated by cooling the sample followed by the addition of 10 mM EDTA in PBS. Up to 90% of the added $^{111}$indium can be incorporated into the preformed liposomes by this method, and the liposomes produce specific activities of up to 300 µCi/mg lipid.

EXAMPLE 4

Vials produced in the process of Example 2 each contained 4.7 ml of the liposome suspension (25 mg liposomes per ml), and contained small unilamellar liposomes having a diameter predominantly of from 50 to 100 nm. The liposomes in these vials were loaded according to the following process. 0.2 ml of 0.1M sodium citrate for injection was added to each vial and mixed well. Following standard radiopharmaceutical procedures to calculate radiopharmaceutical dosages, an amount of $^{111}$indium chloride solution sufficient to yield the prescribed dose of $^{111}$In$^{3+}$ at time of injection was then added. This mixture was then incubated at 80° C. for 30 minutes, followed by cooling to room temperature.

0.1 ml of 0.1M sodium edetate for injection was then added to stop the liposome loading by chelating any excess $^{111}$In. During this process, the radioactive loading efficiency was tested by withdrawing 0.5 ml of the liposome solution prior to terminating the liposome loading procedure, and transferring the solution to a 1.5 ml centrifuge vial containing 0.5 g Chelex 100. The contents of the centrifuge vial were incubated for 5 minutes at room temperature, with occasional mixing, and the total radioactivity of the centrifuged vial was determined using a dose calibrator.

0.5 ml of 0.1 m sodium citrate for injection was then added to the centrifuge vial and then mixed. The vial was then centrifuged for 5 minutes at moderate speed to compact the Chelex 100. 0.5 ml of the supernatant was removed with an appropriate syringe and the radioactivity of the supernatant determined. The calculation for loading efficiency was determined by dividing twice the supernatant radioactivity by the total radioactivity, times 100 to yield percent loading efficiency. In all instances, the loading efficiency was greater than 90%.

Targeting to Ischemic Myocardial Tissue

EXAMPLE 5

An example of the preferential delivery of the small unilamellar liposomes of the invention to ischemic myocardial in the absence of antibody targeting tissue is demonstrated by the use of the labeled liposomes produced in accordance with the procedures in Examples 2 and 4. The liposomes were administered to animals and found to target such tissue.

All animals used were mongrel dogs of either sex (16–20 kg, N=4). The animals were anesthetized before surgery using 30 mg/kg sodium pentobarbital as an i.v. injection. Polyethylene catheters were inserted into a femoral artery and vein for measurement of blood pressure and heart rate, for blood sampling, and for injection of liposomes. The trachea was cannulated and the animal was artificially respired with a Harbard respirator using room air. Eucapnia was maintained and monitored with a Godart-Statham capnograph. A left thoracotomy was performed at the fifth intercostal space, a partial pericardiotomy exposed the heart, and a pericardial cradle was formed. Approximately one cm of the left anterior descending coronary artery (LAD) was isolated just distal to its first major branch and a silk ligature was loosely placed around the vessel. Aortic pressure and heart rate were measured using a Statham P23AA transducer and recorded on a Beckman R-411 recorder. Blood samples obtained from the femoral artery catheter were analyzed electrometrically for blood gases and pH (Radiometer BMS 3 blood gas analyzer).

At this time, 6 mg/kg of $^{111}$In labelled liposomes prepared as in Examples 2 and 4 were injected i.v. After injection of the liposomes into the animals, arterial blood samples were taken 1, 2, 3, 4, 5, 10 minutes and 1, 2, 3, 4, 5, 6 hours post injection and the blood radioactivity was determined later. Ten minutes after liposome injection, the LAD was occluded via the surgical silk snare and the occlusion was continued for 2 hours. At this time, the occlusion was released and the reperfusion was allowed to continue for 4 hours.

At the end of the experiment, blood gas and hemodynamic variables were again s determined and then the heart was removed. The aorta was perfused at a pressure of 100 mm Hg with saline to clear the coronary vessels of blood. The left ventricular free wall was then cut into 6 transmural pieces from the ischemic zone and 6 from the nonischemic zone. These pieces were then divided into subepicardial and subendocardial halves. Samples of the liver and gracilis muscle were also taken. The radioactivity was then determined in both blood and tissue samples using a Hewlett-Packard gamma counter.

All data were analyzed using a paired T-test. The tissue and blood clearance data were expressed as the counts per minute (CPM) of radioactivity per gram of tissue or blood. All data are presented as mean±S.D.

Hemodynamic data are shown in Table 1. All values were within the normal range for dogs. No differences existed for any of these variables during the course of the experiment. No changes in blood gases were seen during the experiment.

The blood clearance data for the liposomes are shown in FIG. 1. As can be seen there is a fast initial clearance followed by a slower clearance phase. The data are expressed as the CPM radioactivity (CPM)/g blood. It is apparent that more than half of the liposomes were cleared from the blood at the end of the experiment.

Data for myocardial tissue clearance of liposomes are shown in Table 2. The data are expressed as the CPM/g tissue. The ischemic region in all animals contained significantly more radioactivity compared to its paired nonischemic region. This difference was 5–10 fold. Within the ischemic zone, the subendocardium contained twice the radioactivity contained in the subepicardium and this difference was significant. The liver was actively clearing liposomes with the CPM/g cleared being $12.34 \times 10^4 \pm 5.49 \times 10^4$ PM/g and skeletal muscle cleared an amount similar to the nonischemic region of the heart $0.11 \times 10^4 \pm 0.01 \times 10^4$ CPM/g.

Summary Biodistribution of Labelled Liposomes in Canine Ischemia

Animals: 16–20 kg dogs—4 studied

Avg. total lipid dose: 6 mg/kg×18 kg=108 mg lipid

Avg. total radioactivity (calculated from avg. blood level at injection): $1300 \times 10^5$ cpm Avg. biodistribution at 6 hrs: cpm/gm ($\times 10^4$)

ischemic subendocardium 2.2±1.1 ischemic subepicardium 1.6±0.9 nonischemic subendocardium 0.26±0.10 nonischemic subepicardium 0.27±0.14

Blood 2.0±0.5

Skeletal muscle 0.11±0.01

Liver 12.3±5.5

Myocardial ischemia and infarction are characterized among other things by an increase in capillary permeability. This increased permeability may allow selective drug delivery to the ischemic region by using appropriately sized liposomes as delivery vehicles. In the present study, the ischemic region localization of radioactivity (and presumably liposomes) was 5–10 times greater compared to the nonischemic myocardium. While I do not wish to be bound by any particular theory, it appears that the liposomes were localized in the ischemic zone due to increased capillary permeability. Interestingly, the ischemic subendocardium tended to localize more liposomes compared to the ischemic subepicardium. This may reflect the fact that the subendocardium is usually more at risk during ischemia. The nonischemic subepicardial-subendocardial difference in localization of liposomes was not significantly different.

The high liver clearance of liposomes is not surprising as this organ is one of the major sites of blood borne particulate removal. This also indicates that the $^{111}$In was bound to liposomes, as $^{111}$In that is free would probably not be cleared by the liver. The estimated labelling efficiency was 70–80%. The nonischemic myocardium and skeletal muscle had relatively low liposome localization.

From the description set forth above, it will be apparent that liposomes having a size of less than about 200 nanometers, preferably 60 to 100 nm will preferentially target active agents such as diagnostic or therapeutic agents to an ischemic myocardial region, and in particular permit the selective localization of the liposomes into the ischemic subendocardium which is typically more at risk, thus facilitating drug delivery to the region of greatest ischemic severity.

From this description the essential characteristics of the invention can be readily ascertained and, without departing from the spirit and scope thereof, the invention can be adapted to various usages. Changes in form and substitution of equivalents are contemplated as circumstances may suggest or render expedient, and although specific terms have been employed herein, they are intended in a descriptive sense and not for purposes of limitation.

TABLE 1

Hemodynamic data for liposome treated animals before and after LAD occlusion and reperfusion.

| | Before Occlusion | After Occlusion + Reperfusion |
|---|---|---|
| Systolic Blood Pressure (mm Hg) | 137 ± 22 | 136 ± 22 |
| Diastolic Blood Pressure (mm Hg) | 116 ± 27 | 100 ± 20 |
| Heart Rate (Beats/min) | 160 ± 28 | 182 ± 21 |

All values are mean ± S.D. (N = 4)

TABLE 2

Localization of $^{111}$In-labelled liposomes in the ischemic and nonischemic myocardium.

| | Ischemic Region ($\times 10^4$) | | Nonischemic Region ($\times 10^4$) | |
|---|---|---|---|---|
| | Subepi-cardium | Subendo-cardium | Subepi-cardium | Subendo-cardium |
| Radioactivity CPM/g | 1.55 ± 0.92 | 2.22* ± 1.14 | 0.27** ± 0.14 | 0.26** ± 0.10 |

All values are mean ± S.D. (N = 4)
*Significantly different from its respective subepicardial region value (P 0.05)
**Significantly different from its respective ischemic region value (P 0.05)

I claim:

1. The method for the delivery of a therapeutic or diagnostic agent to reversible ischemic tissue in a patient, comprising introducing into the patent's bloodstream an amount of unilamellar liposomes containing the agent which are essentially neutral in charge, in the absence of antibodies bound to the liposomes to effect the delivery, the liposomes having a size of less than 200 nanometers and consisting essentially of cholesterol, which is 10 to 50% of total lipid, and a more than 97% chemically pure neutral phospholipid consisting of distearoylphosphatidyl choline, to preferentially deliver the quantity of the agent to the ischemic tissue which is 5 to 10 times greater relative to a nonischemic region by the localization of liposomes in the ischemic tissue.

2. The method of claim 1 in which the ischemic tissue is myocardial tissue and the agent is preferentially delivered to the ischemic tissue rather than to the nonischemic myocardium.

3. The method of claim 1 in which the liposomes have a size of from about 50 to about 100 nanometers.

4. The method of claim 2 in which the liposomes have a size of from about 50 to about 100 nanometers.

\* \* \* \* \*